(12) United States Patent
Miyagi et al.

(10) Patent No.: US 9,615,971 B2
(45) Date of Patent: Apr. 11, 2017

(54) OPHTHALMIC LASER SURGERY APPARATUS AND PROGRAM OF CREATING CONTROL DATA FOR OPHTHALMIC SURGERY

(71) Applicant: NIDEK CO., LTD., Gamagori, Aichi (JP)

(72) Inventors: Tomohiro Miyagi, Aichi (JP); Takayoshi Shibata, Aichi (JP); Masaaki Hanebuchi, Aichi (JP); Naho Murakami, Aichi (JP); Shinya Iwata, Aichi (JP)

(73) Assignee: NIDEK CO., LTD., Aichi (JP)

( * ) Notice: Subject to any disclaimer, the term of this patent is extended or adjusted under 35 U.S.C. 154(b) by 301 days.

(21) Appl. No.: 14/556,385

(22) Filed: Dec. 1, 2014

(65) Prior Publication Data
US 2015/0182380 A1    Jul. 2, 2015

(30) Foreign Application Priority Data
Nov. 29, 2013    (JP) ................. 2013-247289

(51) Int. Cl.
*A61F 9/008*    (2006.01)

(52) U.S. Cl.
CPC ........ *A61F 9/00825* (2013.01); *A61F 9/0084* (2013.01); *A61F 2009/00844* (2013.01); *A61F 2009/00897* (2013.01)

(58) Field of Classification Search
CPC .. A61F 2009/00897; A61F 2009/00844; A61F 9/00825; A61F 9/0084
See application file for complete search history.

(56) References Cited

U.S. PATENT DOCUMENTS

2008/0281303 A1    11/2008    Culbertson et al.
2011/0028958 A1    2/2011    Raksi et al.

FOREIGN PATENT DOCUMENTS

| JP | 201291053 A | 5/2012 |
| JP | 2013-78399 A | 5/2013 |
| WO | 2010136050 A1 | 12/2010 |

OTHER PUBLICATIONS

Communication issued on Apr. 29, 2015 by the European Patent Office in related Application No. 14195368.7.

*Primary Examiner* — Gary Jackson
*Assistant Examiner* — Scott T Luan
(74) *Attorney, Agent, or Firm* — Sughrue Mion, PLLC (57) ABSTRACT

An ophthalmic laser surgery apparatus for treating an eye of a patient includes: a laser light source configured to emit the pulse laser light; an objective lens configured to condense the pulse laser light emitted from the laser light source on the tissue to cause a photodistuption of the tissue; a scanner configured to scan a condensing position of the pulse laser light condensed by the objective lens; and a controller configured to control the scanner to adjust speed of scanning the condensing position depending on a size of the photodisruption which fluctuates in according to an aberration which fluctuates according to a change in the condensing position.

7 Claims, 3 Drawing Sheets

ABERRATION : SMALL ← | → ABERRATION : LARGE

OPHTHALMIC LASER SURGERY APPARATUS AND PROGRAM OF CREATING CONTROL DATA FOR OPHTHALMIC SURGERY

CROSS REFERENCE TO RELATED APPLICATION

This application is based upon and claims the benefit of priority of Japanese Patent Application No. 2013-247289 filed on Nov. 29, 2013, the contents of which are incorporated herein by reference in its entirety.

BACKGROUND

The present disclosure relates to an ophthalmic laser surgery apparatus for treating the eyes of a patient by condensing pulse laser light on a tissue of the eyes of a patient, and to a program of creating control data for an ophthalmic surgery.

In the related art, a technique for treating the eyes of a patient by causing a plurality of photodisruptions in a tissue by condensing pulse laser light on each of a plurality of target positions in the eyes of a patient has been proposed. For example, an ophthalmic laser surgery apparatus disclosed in JP-A-2013-78399 includes a laser light source and scanning means (laser irradiation unit). The laser light source intermittently generates pulse laser light. The scanning means scans (moves) a condensing position on which the pulse laser light is condensed. A photodisruption is caused by an interaction caused between light and a tissue in the condensing position, and the tissue is severed (destroyed). The tissue is treated by scanning the condensing position such that the plurality of photodisruptions are appropriately disposed.

SUMMARY

If a condensing position is changed by driving the scanning means, an aberration that occurs in an optical path of pulse laser light fluctuates. The aberration influences fluence (amount of energy per unit area) of the pulse laser light in the condensing position. If the fluence fluctuates, the size of a photodisruption generated in a tissue fluctuates. Accordingly, the size of the photodisruption fluctuates in accordance with the change in the condensing position.

In some cases, the quality of a surgery deteriorates if the size of the photodisruption fluctuates in accordance with the change in the condensing position. For example, there could be a case where a region in which the severing caused by the plurality of photodisruptions is insufficient is generated, due to the fluctuation in the size of the photodisruption. In addition, there is a possibility that the plurality of photodisruptions are excessively overlapped, and therefore, the quality of the severing deteriorates.

A typical object of the present disclosure is to provide an ophthalmic laser surgery apparatus and a program of creating control data for an ophthalmic surgery which can suppress deterioration of the quality of a surgery by reducing the influence of an aberration accompanied by the change in a condensing position.

An aspect of the present disclosure provides the following arrangements:

An ophthalmic laser surgery apparatus for treating an eye of a patient, the ophthalmic laser surgery apparatus comprising:

a laser light source configured to emit the pulse laser light;

an objective lens configured to condense the pulse laser light emitted from the laser light source on the tissue to cause a photodistuption of the tissue;

a scanner configured to scan a condensing position of the pulse laser light condensed by the objective lens; and a controller configured to control the scanner to adjust speed of scanning the condensing position depending on a size of the photodisruption which fluctuates in according to an aberration which fluctuates according to a change in the condensing position.

A method of creating control data for controlling an ophthalmic laser surgery apparatus for treating an eye of a patient by causing a photodisruption in a tissue by condensing pulse laser light on the tissue of the eyes of the patient, the method comprising:

creating control data which causes the ophthalmic laser surgery apparatus to adjust speed of scanning a condensing position using a scanner depending on a size of the photodisruption which fluctuates in response to an aberration accompanied by a change in the condensing position.

A non-transitory computer readable recording medium storing a computer readable instruction for creating control data that controls an ophthalmic laser surgery apparatus which treats eyes of a patient by causing a photodisruption in a tissue by condensing pulse laser light on the tissue of the eyes of the patient, the instruction causing a processer of the ophthalmic laser surgery apparatus to execute:

a creation step of creating control data which causes the ophthalmic laser surgery apparatus to adjust speed of scanning a condensing position using a scanner depending on a size of the photodisruption which fluctuates in response to an aberration accompanied by a change in the condensing position.

A method of controlling an ophthalmic laser surgery apparatus for treating an eye of a patient, the method comprising:

emitting the pulse laser light;

condense the emitted pulse laser light on the tissue to cause a photodistuption of the tissue;

scanning a condensing position of the condensed pulse laser light; and controlling the scanner to adjust speed of scanning the condensing position depending on a size of the photodisruption which fluctuates in according to an aberration which fluctuates according to a change in the condensing position.

According to the ophthalmic laser surgery apparatus and the program of creating control data for an ophthalmic surgery which are shown by the present disclosure, it is possible to suppress deterioration of the quality of a surgery by reducing the influence of an aberration accompanied by the change in a condensing position.

DESCRIPTION OF ILLUSTRATIVE EMBODIMENTS

Hereinafter, an illustrative embodiment according to the present disclosure will be described with reference to the accompanying drawings. First, a schematic structure of an ophthalmic laser surgery apparatus 1 of the present embodiment will be described with reference to FIG. 1. Hereinafter, the axis direction of the eyes of a patient E is described as a Z direction, the horizontal direction thereof is described as an X direction, and the perpendicular direction thereof is described as a Y direction, for example. In the drawing, each of the lenses, mirrors, and the like is shown using a member. However, each of the lenses, mirrors, and the like may be configured to have a plurality of optical components.

<Overall Configuration>

Figure 1:
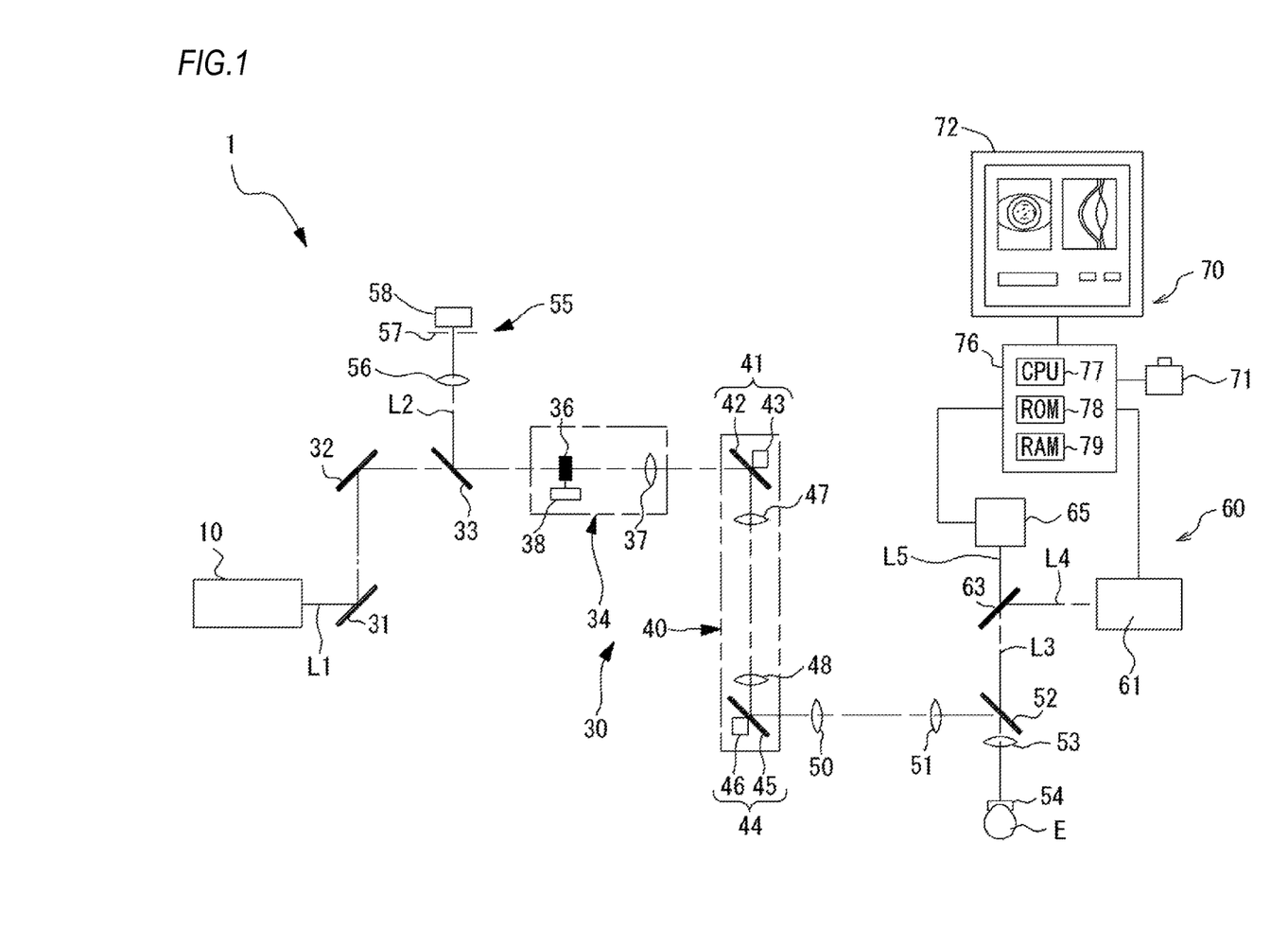
FIG. 1 is a view showing a schematic structure of an ophthalmic laser surgery apparatus 1.

The ophthalmic laser surgery apparatus 1 of the present embodiment is used for treating a tissue of the eyes of a patient E. In the present embodiment, the ophthalmic laser surgery apparatus 1 capable of treating the cornea of the eyes of a patient E is exemplified. However, the technique exemplified in the present embodiment can also be applied to a case of treating other sites (for example, the crystalline lens) of the eyes of a patient E. The ophthalmic laser surgery apparatus 1 of the present embodiment includes a laser light source 10, a scanning unit 30, an objective lens 53, a position detection unit 55, an observing/photographing unit 60, an operation unit 70, and a control unit 76.

<Laser Light Source>

The laser light source 10 emits pulse laser light. In the present embodiment, the pulse laser light emitted from the laser light source 10 is used for inducing plasma in a tissue through a non-linear interaction. The non-linear interaction is an interaction caused by light and a substance and is an action in which a response which is not proportional to the intensity of light (that is, density of photons) appears. The ophthalmic laser surgery apparatus 1 of the present embodiment causes multiple-photon absorption at a condensing position (in some cases, also called a "laser spot") or further on a slightly upstream side of an optical path (optical flux) than the condensing position by condensing (focusing) pulse laser light within a transparent tissue of the eyes of a patient E. The probability that the multiple-photon absorption occurs is not proportional to the intensity of light and becomes non-linear shape. When an excited state is caused by the multiple-photon absorption, bubbles are generated in the tissue. The generated bubbles are gradually absorbed into the tissue, and cutting, destroying and the like of the tissue are performed at the position at which the bubbles were generated. The bubbles are generated through plasma, and therefore, in some cases, are called plasma bubbles. In some cases, the above-described phenomenon is also called a photodisruption. In the photodisruption caused by the non-linear interaction, heat using laser light hardly affects the periphery of the condensing position. Accordingly, it is possible to perform microscopic treatment. The photodisruption efficiently occurs with lower energy as the pulse width of the pulse laser light becomes smaller.

<Scanning Unit>

The scanning unit 30 scans the condensing position of the pulse laser light which is condensed by the objective lens 53 (details of which are to be described later) by scanning the pulse laser light. That is, the scanning unit 30 moves the condensing position of the pulse laser light to a target position. The scanning unit 30 of the present embodiment includes a Z scanner 34 and an XY scanner 40.

The Z scanner 34 of the present embodiment includes a concave lens 36, a convex lens 37, and a driving portion 38. The driving portion 38 moves the concave lens 36 along an optical axis L1. The divergence state of a beam passed through the concave lens 36 changes due to the movement of the concave lens 36. As a result, the condensing position (laser spot) of the pulse laser light moves in the Z direction.

The XY scanner 40 of the present embodiment includes an X scanner 41, a Y scanner 44, and lenses 47 and 48. The X scanner 41 scans the pulse laser light in an X direction by oscillating a galvano mirror 42 using a driving portion 43. The Y scanner 44 scans the pulse laser light in a Y direction by oscillating a galvano mirror 45 using a driving portion 46. The lenses 47 and 48 take the two galvano mirrors 42 and 45 as a conjugate pair.

Mirrors 31 and 32 and a hole mirror 33 are provided between the laser light source 10 and the Z scanner 34. The mirrors 31 and 32 induce the pulse laser light to be emitted from the laser light source 10. The hole mirror 33 makes the optical axis L1 of the pulse laser light and an optical axis L2 of the position detection unit 55 (to be described later) coincide with each other. In addition, lenses 50 and 51 and a beam combiner 52 are provided between the XY scanner 40 and the objective lens 53. The lenses 50 and 51 relay the pulse laser light. The beam combiner 52 makes the optical axis L1 of the pulse laser light and an optical axis L3 of the observing/photographing unit 60 (to be described later) coincide with each other.

The configuration of the scanning unit 30 can be appropriately modified. For example, the lenses 47 and 48 between the X scanner 41 and the Y scanner 44 can be omitted. The ophthalmic laser surgery apparatus 1 may perform scanning of the pulse laser light in an X-Y direction using acousto-optical elements (AOM, AOD) and the like which deflect the pulse laser light instead of the galvano mirrors 42 and 45. Scanning in one direction may be performed using a plurality of elements. A resonant scanner, a polygon mirror, and the like may also be used. The position of the Z scanner 34 may be on a downstream side of the XY scanner 40. A plurality of Z scanners may be equipped in the ophthalmic laser surgery apparatus 1. Other changes can also be made to the scanning unit 30.

<Objective Lens>

The objective lens 53 is provided on an optical path between the scanning unit 30 and the eyes of a patient E. The objective lens 53 condenses the pulse laser light passed through the scanning unit 30 on the tissue of the eyes of a patient E. In the present embodiment, when the cornea of the eyes of a patient E is to be treated, the pulse laser light emitted from the objective lens 53 is condensed on the tissue of the eyes of a patient E through a contact lens 54. In the contact lens 54, a surface coming into contact with the eyes of a patient E is formed on a predetermined curved surface or planar surface. The surface of the cornea of the eyes of a patient E is fixed in a predetermined shape by the contact lens 54 being flattened to the eyes of a patient E. The interface placed on the eyes of a patient E is not particularly limited to the contact lens 54. For example, it is also possible to use a liquid-immersion interface having a structure, in which a sucked and fixed cup is filled with a liquid, for the eyes of a patient E instead of the contact lens 54.

<Position Detection Unit>

The position detection unit 55 is used for detecting the position of the eyes of a patient E with respect to the scanning unit 30. The ophthalmic laser surgery apparatus 1 of the present embodiment makes the condensing position, on which the pulse laser light is condensed, correspond to a tomographic image (details of which are to be described later) by detecting the position of the eyes of a patient E with respect to the scanning unit 30. It is possible to set control data for controlling the scanning unit 30 or the like using the tomographic image by making the condensing position correspond to the tomographic image.

In the present embodiment, a portion of an optical system through which pulse laser light passes also serves as an optical system of the position detection unit 55. The position detection unit 55 includes a hole mirror 33, a condensing lens 56, an aperture plate 57, and a light receiving element 58. The hole mirror 33 transmits light incident on the center of the hole mirror and reflects light which is reflected by the eyes of a patient E along the optical axis L2. The condensing lens 56 condenses the light reflected by the hole mirror 33 on an aperture of the aperture plate 57. The aperture plate 57 is a confocal aperture plate having an aperture in the center thereof. The aperture of the aperture plate 57 is disposed so as to have a conjugated relationship with the condensing position (position of the laser spot) of the pulse laser light in the eyes of a patient E. The light receiving element 58 receives light which has passed through the aperture of the aperture plate 57. The ophthalmic laser surgery apparatus 1 of the present embodiment adjusts the output of laser light emitted from the laser light source 10 such that the laser light does not cause a photodisruption at the condensing position when detecting the position of the eyes of a patient E. The ophthalmic laser surgery apparatus 1 receives light using reflected light from the eyes of a patient E using the light receiving element 58 while moving the condensing position in a three-dimensional direction using the scanning unit 30.

The configuration for detecting the position of the eyes of a patient E with respect to the scanning unit 30 can be appropriately modified. For example, irradiation light and reflected light may be separated using a polarization beam splitter instead of the hole mirror 33. In addition, the ophthalmic laser surgery apparatus 1 may irradiate a sample substance or the like with pulse laser light and detect an actual condensing position in the sample substance or the like using a tomographic image (to be described later).

<Observing/Photographing Unit>

The observing/photographing unit 60 makes an operator observe the eyes of a patient E and photographs a tissue to be treated. For example, the observing/photographing unit 60 of the present embodiment includes an OCT unit 61 and a front observation unit 65. The optical axis L3 of the observing/photographing unit 60 is made coaxial with the optical axis L1 of the pulse laser light by the beam combiner 52. The optical axis L3 is branched into an optical axis L4 of the OCT unit 61 and an optical axis L5 of the front observation unit 65 by a beam combiner 63.

The OCT unit 61 acquires a tomographic image of a tissue of the eyes of a patient E using a technique of light interference. In detail, the OCT unit 61 of the present embodiment includes a light source, a light splitter, a reference optical system, a scanner, and a detector. The light source emits light for acquiring the tomographic image. The light splitter divides light emitted from the light source into reference light and measurement light. The reference light is incident on the reference optical system and the measurement light is incident on the scanner. The reference optical system has a configuration in which the optical path length difference between the measurement light and the reference light is changed. The scanner scans the measurement light onto the tissue in a two-dimensional direction. The detector detects the interference states of the measurement light which has reflected from the tissue and the reference light which has passed through the reference optical system. The ophthalmic laser surgery apparatus 1 scans the measurement light and detects the interference states of the reflected measurement light and interference light to obtain information of the tissue in a depth direction. The tomographic image of the tissue is acquired based on the acquired information in the depth direction. The ophthalmic laser surgery apparatus 1 of the present embodiment makes the position on which the pulse laser light is condensed correspond to the tomographic image of the eyes of a patient E which has been photographed before the surgery. As a result, the ophthalmic laser surgery apparatus 1 can create control data for controlling an operation (for example, an operation of the driving portions 38, 43, and 46) of radiating the pulse laser light, using the tomographic image. It is possible to use various configurations for the OCT unit 61. For example, any one of SS-OCT, SD-OCT, TD-OCT, and the like may be employed as the OCT unit 61.

The front observation unit 65 acquires a frontal image of the eyes of a patient E. The front observation unit 65 of the present embodiment photographs the eyes of a patient E irradiated with visible light or infrared light and displays the result on a monitor 72 (to be described later). The operator can observe the eyes of a patient E from the front by viewing the monitor 72.

<Operation Unit>

The operation unit 70 receives inputs of various operation instructions from the operator. For example, the operation unit 70 of the present embodiment includes an operation portion 71 which is provided with various operation buttons, and a touch panel which is provided on the surface of the monitor 72. However, other configurations such as a joystick, a keyboard, and a mouse can also be employed as the operation unit 70. It is possible to display, for example, various images such as a frontal image of the eyes of a patient E, a tomographic image of a tissue, and various operation menus on the monitor 72.

<Control Unit>

The control unit 76 is provided with a CPU 77, a ROM 78, a RAM 79, a non-volatile memory (not shown), and the like. The CPU 77 performs various controls (for example, control of control data creation to be described later, control of the laser light source 10, control of the scanning unit 30, and control of adjusting the speed of scanning the condensing position) of the ophthalmic laser surgery apparatus 1. The ROM 78 stores various programs for controlling the operation of the ophthalmic laser surgery apparatus 1, an initial value, and the like. The RAM 79 temporarily stores various pieces of information. The non-volatile memory is a non-transient storage medium which can hold the stored contents even if power supply is interrupted.

<Relationship Between Aberration Occurring in Optical Path and Quality of Surgery>

The relationship between the aberration occurring in the optical path of the pulse laser light and the quality of a surgery will be described. Various aberrations can occur in at least any one of a lens, a mirror, a scanner, a tissue of the eyes of a patient, and the like which are positioned at the optical path (in detail, an optical path from the laser light source 10 to the condensing position) of the pulse laser light. When the condensing position of the pulse laser light which has been scanned by the scanning unit 30 is changed, the aberration fluctuates. For example, in some cases, an image surface curvature, astigmatism, and the like fluctuate depending on the distance between the center of the optical flux of the pulse laser light which has scanned by the XY scanner 40 in the X-Y direction, and the optical axis L1 which passes through the center of each of the optical elements such as a lens. When the condensing position is scanned in the Z direction, in some cases, a spherical aberration, a chromatic aberration, and the like fluctuate. In addition, when the position on which the pulse laser light is condensed changes in the eyes of a patient E, in some cases, the aberration caused by the tissue of the eyes of a patient E fluctuates. When the aberration fluctuates, the condensing state (for example, fluence) of the pulse laser light is changed. As a result, in some cases, a photodisruption 5 (for example, the size of the photodisruption 5) occurring at the condensing position or in the vicinity thereof changes.

Figure 2:
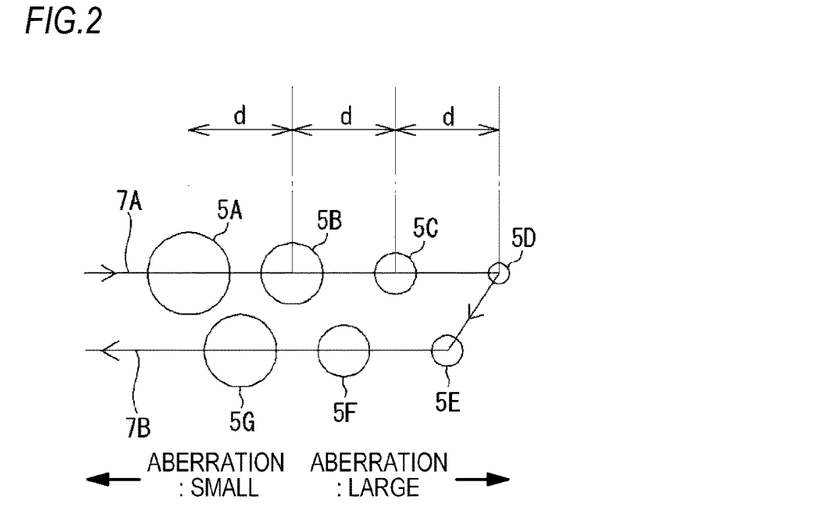
FIG. 2 is a view schematically showing an example of a formation state of photodisruptions 5 in a case of scanning a condensing position by making the energy of pulse laser light, a repetition frequency, and a scanning speed constant.

FIG. 2 is a view schematically showing an example of a formation state of a photodisruption 5 in a case of making the energy of condensed pulse laser light, a repetition frequency, and a scanning speed constant, and in a case in which an aberration fluctuates depending on the condensing position. In FIG. 2, the gaps between and the sizes of photodisruptions 5, the gaps between the scanning routes 7, and the like are shown in different scales from the actual scales for easy understanding of the formation state of the photodisruption 5. In the example shown in FIG. 2, the aberration occurring in the optical path becomes larger as the condensing position approaches from the left side to the right side of the drawing. In addition, the route of scanning the condensing position first advances to the right along an upper scanning route 7A, is bent downward in the drawing, and further advances to the left along a lower scanning route 7B. The gaps between the upper scanning route 7A and the lower scanning route 7B are constant.

The speeds of scanning the condensing positions using the scanning unit 30 are constant and the repetition frequency is also constant, and therefore, all of the distances between centers of two adjacent condensing positions along the scanning routes 7 become a constant distance d. However, in the example shown in FIG. 2, the sizes of photodisruptions 5 (bubbles) generated at the condensing position or in the vicinity thereof fluctuate due to the aberration which fluctuates depending on the condensing position. In detail, the sizes of four photodisruptions 5 positioned on the upper scanning route 7A become smaller in order of 5A, 5B, 5C, and 5D as the aberration close to the right side becomes larger. The sizes of three photodisruptions 5 positioned on the lower scanning route 7B become larger in order of 5E, 5F, and 5G as the aberration close to the left side becomes smaller.

Even if the distances between centers of the photodisruptions 5 on the scanning route 7 are constant, when the sizes of the photodisruptions 5 fluctuate, excessive separation or excessive approach of the plurality of photodisruptions 5 can occur. That is, the density occupied by the volume of the photodisruptions 5 with respect to unit volume changes depending on the site. In addition, in the example shown in FIG. 2, the gaps between the two adjacent scanning routes 7A and 7B are constant in spite of the sizes of the photodisruptions 5 fluctuating. As a result, the minimum distance between the photodisruptions 5 on the scanning routes 7A and the photodisruptions 5 on the scanning routes 7B changes depending on the site. Accordingly, the density of the photodisruptions 5 changes more depending on the site. When the density of the photodisruptions 5 does not become constant, there is a possibility that the quality of the severing due to the photodisruptions 5 may be degraded. The ophthalmic laser surgery apparatus 1 of the present embodiment suppresses the degradation of the quality of the surgery by reducing the above-described influence of the aberration. Hereinafter, processing which is executed by the ophthalmic laser surgery apparatus 1 of the present embodiment will be described.

<Processing>

Figure 3:
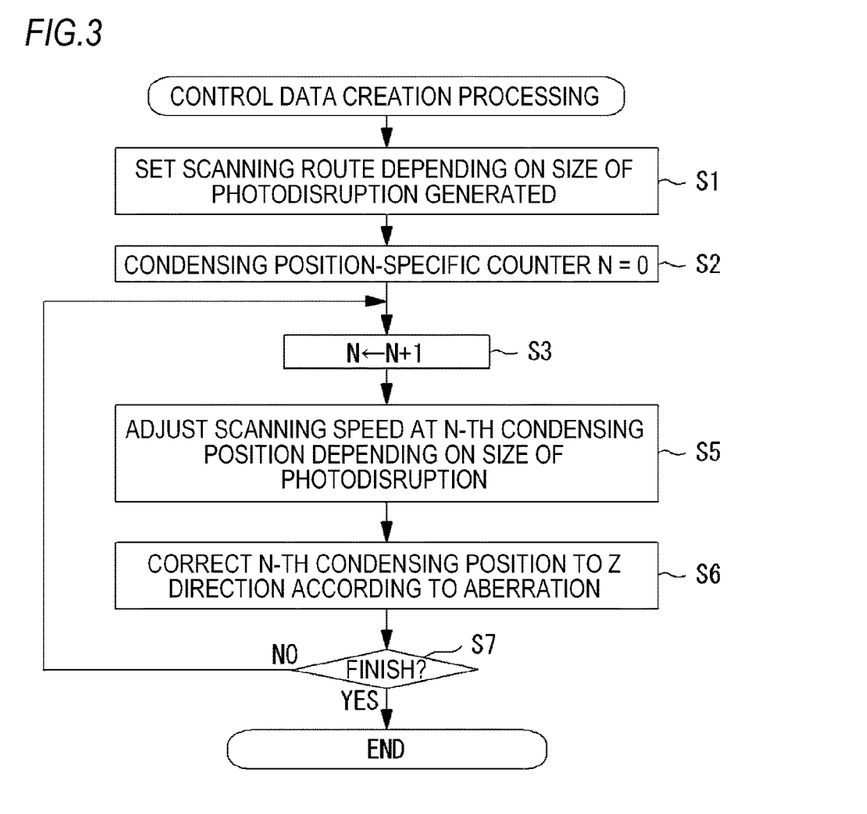
FIG. 3 is a flowchart of control data creation processing which is executed by a CPU 77.

Control data creation processing which is executed by the ophthalmic laser surgery apparatus 1 of the present embodiment will be described with reference to FIG. 3. The control data is data for determining control contents during a surgery using the control unit 76. The control data creation processing exemplified in FIG. 3 is executed by the CPU (processor) 77 of the control unit 76 when an instruction to create control data has input through the operation portion 71 or the like. The CPU 77 executes the control data creation processing shown in FIG. 3 in accordance with a program of creating control data for an ophthalmic surgery which is stored in the ROM 78 or a non-volatile memory.

First, scanning routes 7 of condensing positions are set depending on the size of a photodisruption 5 generated at each of the condensing positions (or in the vicinity thereof) (S1). The CPU 77 of the present embodiment creates control data such that the gaps between the adjacent scanning routes 7 are shortened as the sizes of the photodisruptions 5 fluctuating become smaller due to the aberration accompanied by the change in the condensing position. For example, in the present embodiment, the CPU 77 acquires information of the sizes (for example, diameters) of photodisruptions 5 generated at each position and determines the gap of the scanning routes 7 such that the sizes of photodisruptions 5 and the gaps between the scanning routes 7 are proportional to each other.

A method of acquiring information on the sizes of the photodisruptions 5 generated at each position will be described. In the ophthalmic laser surgery apparatus 1 of the present embodiment, data (for example, table data) or an algorithm, which determines the relationship between the condensing position controlled by the scanning unit 30, and the size (for example, the size of a bubble) of the photodisruption 5 at each condensing position for each energy source of the pulse laser light, is used. For example, the maximum size of a bubble before being absorbed into a tissue may be acquired as information of the size of a photodisruption 5. In addition, even if the condensing position is the same, in some cases, the sizes of the photodisruptions 5 fluctuate due to the tissue or the like. In this case, an average value of the sizes of the photodisruptions 5 generated at each condensing position may be acquired.

For example, a developer condenses pulse laser light on a plurality of target positions of a sample substance (for example, PMMA, water, the animal eyes) using a plurality of different energy sources and measures the sizes of the photodisruptions 5 generated as a result using a tomographic image or the like. Table data, in which the energy of the pulse laser light, the condensing position, and the sizes of the generated photodisruptions are made to correspond to each other using the measured result, may be previously created and stored in the ROM 78 or the like. In this case, an influence of the aberration, which can occur depending on the condensing position, on the photodisruptions 5 is also reflected in the table data.

In addition, the developer may set an algorithm for calculating the sizes of the photodisruptions 5 at each position in accordance with the sizes of the aberrations that fluctuate depending on the condensing position, to be programmed in advance. Approximate values of the sizes of the aberrations can be represented using one or plural kinds of a root mean square (RMS) wavefront error, a Strehl ratio, a diameter of the condensing position (laser spot), and the like. For example, it is possible to use a function "RMS=f(z,r,ϕ)" for calculating the approximate values of RMS corresponding to the condensing position using a Z coordinate (z) of the condensing position, a distance (r) from a Z axis, and an azimuth angle (ϕ). In addition, it is possible to use a function "B=f(RMS)" for calculating the sizes (B) of the photodisruptions 5 at the condensing position using the approximate values of RMS at the condensing position. The sizes (B) of the photodisruptions 5 determined by the algorithm become a size considering the influence of the aberration generated while condensing the pulse laser light on the condensing position. In addition, the developer may measure the aberration while condensing the pulse laser light on each condensing position using a wavefront sensor, a beam profiler, and the like to create an algorithm or table data using the measured result. The CPU 77 can acquire information on the sizes of the photodisruptions 5 at each position using the data or the algorithm. The CPU 77 may acquire information on the sizes of the photodisruptions 5 considering other pieces of information. For example, the ophthalmic laser surgery apparatus 1 of the present embodiment can acquire information on the sizes of the photodisruptions 5 depending on the condensing position also considering the degree of opacity of the eyes of a patient E due to cataracts or the like.

Figure 4:
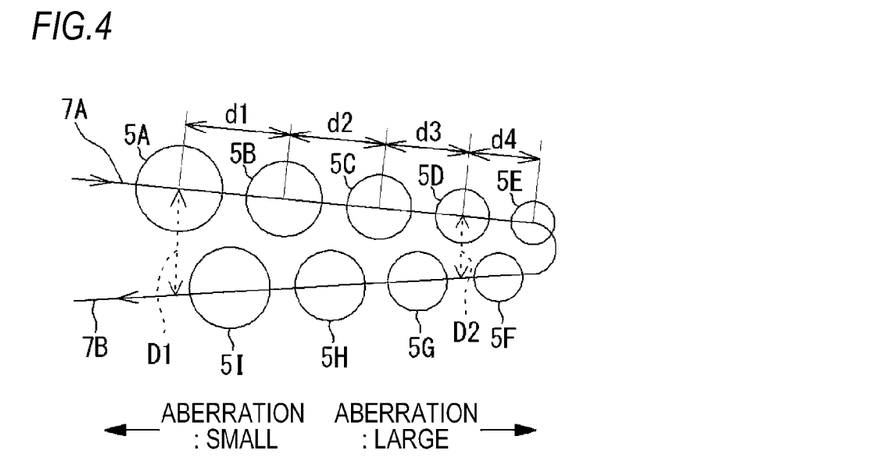
FIG. 4 is a view schematically showing an example of a formation state of photodisruptions 5 in a case in which the ophthalmic laser surgery apparatus 1 of the present embodiment scans the condensing position.

The relationship between the sizes of the photodisruptions 5, and the gaps between the scanning routes 7 set in the present embodiment will be described with reference to FIG. 4. FIG. 4 is a view showing an example of a formation state of photodisruptions 5 in a case in which the ophthalmic laser surgery apparatus 1 of the present embodiment scans a condensing position. In the example shown in FIG. 4, similarly to the case of FIG. 2, the energy of the condensed pulse laser light and the repetition frequency are constant. In addition, similarly to the case of FIG. 2, the aberration occurring in the optical path becomes larger as the condensing position approaches from the left side to the right side of the drawing. In contrast, in the example shown in FIG. 4, the gaps between the scanning routes 7 and the scanning speed are different from those in the case of FIG. 2.

In FIG. 4, the sizes of photodisruptions 5 are gradually reduced due to the aberration as the condensing position approaches the right side of the drawing. The CPU 77 sets the scanning routes 7 such that the gaps between an upper scanning route 7A and a lower scanning route 7B are shortened as the condensing position approaches the right side of FIG. 4. As a result, a gap D1 between the scanning routes 7A and 7B at a largest position of the photodisruption 5A is larger than a gap D2 between the scanning routes 7A and 7B at a position of the photodisruption 5D. When a condensing position is scanned in accordance with the scanning routes 7 which have been set as above, the minimum distances (minimum distances between outer periphery surfaces of two bubbles) between each of the photodisruptions 5A to 5E generated along the upper scanning route 7A and each of the photodisruptions 5F to 5I generated along the lower scanning route 7B constantly become closer regardless of fluctuation in the sizes of the photodisruptions 5. Accordingly, the density of the photodisruptions 5 is uniformly approximated compared to the case in which the gaps between the scanning routes 7 are constant.

The method of setting the scanning routes 7 can be appropriately modified. For example, it is not necessary that the sizes of the photodisruptions 5 and the gaps between the scanning routes 7 always be proportional to each other. In addition, the CPU 77 can set the scanning routes 7 without directly acquiring information on the sizes of the photodisruptions 5. For example, the gaps between the scanning routes 7 may be previously set depending on the position so as to shorten the gaps between the scanning routes 7 as the sizes of the photodisruptions 5 become smaller. In addition, as described above, the aberration influences the sizes of the photodisruptions 5. Accordingly, a single data piece and algorithm (for example, the above-described function "RMS=f(z,r,ϕ)") for determining each position and the size of the aberration at the position are also included in the data and the algorithm determining the sizes of the photodisruptions 5.

Returning to the description of FIG. 3, when the scanning routes 7 are set (S1), the value of a condensing position-specific counter N is initialized to "0" (S2). For example, in the control data of the present embodiment, data for adjusting the speed of scanning using the scanning unit 30 or the like corresponds to each condensing position. The condensing position-specific counter N is used for specifying each of a plurality of condensing positions. Next, "1" is added to the condensing position-specific counter N (S3).

Next, the scanning speed at an N-th condensing position is adjusted depending on the sizes of the photodisruptions 5 (S5). As a result, the gap between a photodisruption 5 generated at an N-th condensing position and a photodisruption 5 on a scanning route 7 which is adjacent to the N-th photodisruption 5 becomes an appropriate gap depending on the size of the photodisruption.

In detail, in the present embodiment, the scanning speed is adjusted such that the speed of scanning the condensing position is decreased as the sizes of the photodisruption 5 become smaller. In this case, even if the sizes of the photodisruptions 5 become smaller due to the aberration, the distances between centers of two adjacent photodisruptions 5 on the scanning routes 7 become short, and therefore, excessive separation between the two photodisruptions 5 is suppressed. In addition, even if the sizes of the photodisruptions 5 become larger due to the aberration, the distances between the centers of two adjacent photodisruptions 5 on the scanning routes 7 become long, and therefore, excessive approach or repetition of the two photodisruptions 5 is suppressed.

In addition, in the present embodiment, the above-described data or the algorithm for determining the relationship between each condensing position and the size (for example, the size of the bubble) of the photodisruption 5 is used to adjust the scanning speed. For example, the CPU 77 determines a desired center position of an N-th photodisruption 5 using the above-described data or the algorithm based on the position and the size of a photodisruption 5 generated at an (N−1)-th condensing position, and the gap between the desired photodisruptions 5. The scanning speed (in the present embodiment, the driving speed of the Z scanner 34 and the XY scanner 40) is set such that the determined desired center position becomes the center of the N-th condensing position. Even when the scanning routes 7 are not linear, it is natural that it is possible to apply the technique exemplified in the present disclosure thereto.

As shown in FIG. 4, in the present embodiment, the speed of scanning the condensing position is decreased as the size of the photodisruption 5 becomes smaller due to the aberration. For example, five photodisruptions 5A to 5E on the scanning route 7A shown in FIG. 4 sequentially become smaller. However, the speed of scanning the condensing position gradually decreases. Accordingly, each of gaps d1 to d4 between two adjacent photodisruptions among the photodisruptions 5A to 5E is sequentially shortened. As a result, the density of a plurality of photodisruptions 5 adjacent to the scanning routes 7 is uniformly approximated.

Next, the N-th condensing position is corrected to be at least in a direction along the optical axis L1 of the pulse laser light according to the aberration. The phenomenon in which the condensing position is changed according to the aberration will be described with reference to FIG. 5. In the two examples shown in FIG. 5, only the sizes of aberrations generated in optical paths of pulse laser light are different from each other and other parameters (for example, a numerical aperture NA, energy of condensed pulse laser light, and the like) are the same as each other. In the example on the left side of FIG. 5, multiple-photon absorption occurs in a condensing position (laser spot) 82 to cause a photodisruption 5X. On the contrary, in the example on the right side of FIG. 5, the aberration is smaller than that of the example on the left side thereof. As a result, fluence (amount of energy per unit area) of a laser pulse exceeds a threshold value for causing multiple-photon absorption on an upstream side of an optical path (optical flux) rather than on the condensing position 82 in a case in which the laser pulse is not absorbed by a tissue. That is, in the example on the right side of FIG. 5, the multiple-photon absorption occurs further on the upstream side of the optical path than the condensing position 82. In addition, in the example shown in FIG. 5, the optical flux of the pulse laser light extends parallel to the optical axis (Z direction).

Figure 5:
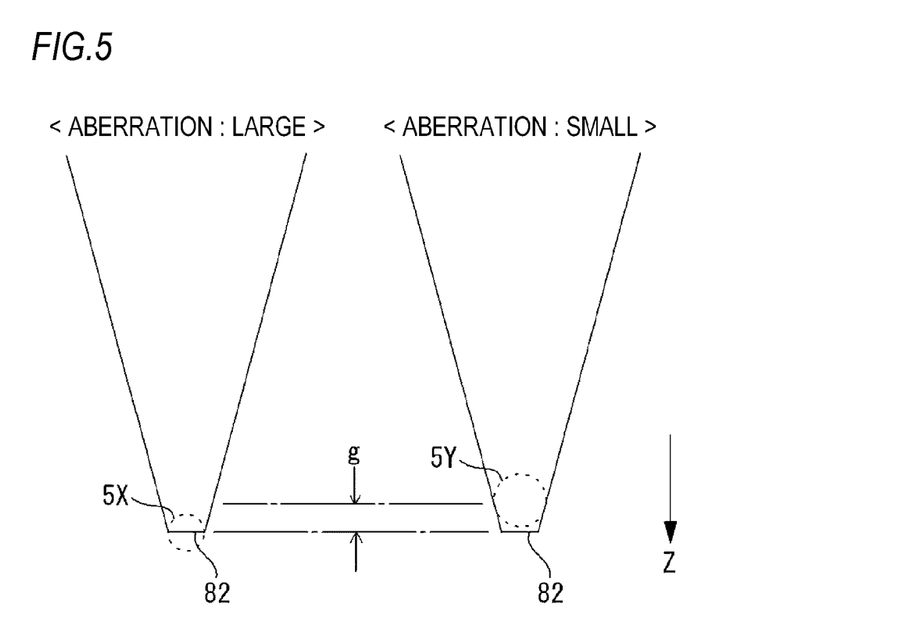
FIG. 5 is an explanatory view for describing a change in positions of photodisruptions 5X and 5Y caused by fluctuation in an aberration.

Accordingly, the position of an optical axis 5Y occurring in the example on the right side of FIG. 5 is deviated to the upstream side by a distance g in a direction (Z direction) parallel to the optical path of the pulse laser light compared to the position of the photodisruption 5X occurring in the example on the left side thereof. In some cases, the position of the photodisruption 5 is changed due to the change in the position, at which the multiple-photon absorption occurs, according to the aberration as described above.

In the present embodiment, the CPU 77 corrects the condensing position of the pulse laser light at least to the Z direction in consideration of the fluctuation in the position of the photodisruption 5 caused by the fluctuation in the aberration and creates control data (S6). That is, when the pulse laser light emitted from the objective lens 53 extends parallel to the optical axis L1, the CPU 77 corrects the condensing position to the Z direction. When the direction of the optical flux of the pulse laser light emitted from the objective lens 53 is not parallel to the optical axis L1, the CPU 77 corrects the condensing position in each of the X, Y, and Z directions. As a result, the photodisruption 5 occurs at a target position. For example, when scanning the condensing position such that a curved surface is severed, the CPU 77 corrects the condensing position such that the photodisruption 5 occurs on a curved surface to be severed.

Next, it is determined whether the processing (that is, the processing with respect to all the scanning routes 7 set in S1) is finished with respect to all of the condensing positions (S7). When the processing is not finished with respect to all of the condensing positions (S7: NO), the processing returns to S2 and processing with respect to the next condensing position is executed (S2 to S6). When the processing with respect to all of the condensing position is finished (S7: YES), the control data creation processing is finished. FIG. 4 is an example in which the ophthalmic laser surgery apparatus 1 executes a treatment in accordance with the control data created through the control data creation processing (refer to FIG. 3). The ophthalmic laser surgery apparatus 1 actively adjusts the scanning speed in a process of performing a series of treatments. That is, it is not necessary to suspend the treatment every time when adjusting the scanning speed.

As described above, the ophthalmic laser surgery apparatus 1 of the present embodiment adjusts the speed of scanning the condensing position using the scanning unit 30 depending on the sizes of the photodisruptions 5 fluctuating caused by the aberration accompanied by the change in the condensing position. It is possible to adjust the distances between the centers of two adjacent photodisruptions 5 by adjusting the speed of scanning the condensing position. Accordingly, the ophthalmic laser surgery apparatus 1 can dispose a plurality of photodisruptions 5 at appropriate intervals depending on the sizes of the fluctuating photodisruptions 5. Accordingly, it is possible to suppress deterioration of the quality of a surgery by reducing the influence of the aberration accompanied by the change in the condensing position.

In detail, the ophthalmic laser surgery apparatus 1 of the present embodiment adjusts the speed of scanning using the scanning unit 30 such that the speed of scanning the condensing position is decreased as the sizes of the photodisruptions 5 become smaller. In this case, even if the sizes of the photodisruptions 5 fluctuate due to the aberration, the distances between the centers of two adjacent photodisruptions 5 along the scanning routes 7 become a distance suitable for the sizes of the fluctuating photodisruptions 5. Accordingly, the ophthalmic laser surgery apparatus 1 can efficiently suppress excessive separation, excessive approach, and the like of the photodisruptions 5 caused by the aberration.

The ophthalmic laser surgery apparatus 1 of the present embodiment sets the scanning routes 7 such that the gaps between the scanning routes 7 are shortened as the sizes of the photodisruptions 5 become smaller. In this case, even when the sizes of the photodisruptions 5 fluctuate due to the aberration, the distance between the centers of a photodisruption 5 on a scanning route 7 and a photodisruption 5 on a scanning route 7 which is adjacent to the scanning route 7 also becomes an appropriate distance. Accordingly, the ophthalmic laser surgery apparatus 1 can efficiently suppress the excessive separation, the excessive approach, and the like of the photodisruptions 5 caused by the aberration.

The ophthalmic laser surgery apparatus 1 of the present embodiment controls the scanning using the data or the algorithm for determining the relationship between the condensing position and the size of the photodisruption 5 at each condensing position. As a result, the photodisruptions 5 are more appropriately disposed and the quality of the surgery is further improved. In addition, the ophthalmic laser surgery apparatus 1 of the present embodiment can correct the condensing position to be at least in a direction along the optical axis L1 depending on the aberration which fluctuates according to the change in the condensing position. Accordingly, the photodisruptions 5 are appropriately disposed.

For example, it can be considered that the fluctuation in the sizes of the photodisruptions is controlled by adjusting the energy of the pulse laser light using an optical modulator in consideration of the fluctuation in the aberration accompanied by the change in the condensing position. However, in this case, the use of a configuration for adjusting the energy of the pulse laser light is required. In addition, it can also be considered that the repetition frequency of the pulse laser light is adjusted in consideration of the fluctuation in the aberration. However, in this case, it is necessary to have a configuration (for example, a configuration for suppressing the influence of dispersion of a laser light source 10 caused by an amplifier due to the change in the repetition frequency) for smoothly changing the repetition frequency. On the contrary, the ophthalmic laser surgery apparatus 1 of the present embodiment can reduce the influence of the aberration accompanied by the change in the condensing position based on a principle completely different from the principle used for adjusting the energy of the pulse laser light and the repetition frequency. Accordingly, it is possible to reduce the influence of the aberration without changing the energy or the repetition frequency. In addition, it is also possible to further reduce the influence of the aberration by combining the method of changing the energy or the repetition frequency and the method exemplified in the present embodiment.

The contents disclosed in the above-described embodiment are merely examples. Accordingly, it is possible to change the contents disclosed in the above-described embodiment. Hereinafter, a modification example of the above-described embodiment will be described. At least a portion of the modification example to be described below can employ the configuration exemplified in the above-described embodiment. Accordingly, in the description of the below modification example, a configuration which is different from the configuration of the above-described embodiment will be mainly described and the description of the portion in which it is possible to employ the same configuration as that of the above-described embodiment will be omitted or be simplified.

In the above-described embodiment, the case, in which each energy source of the plurality of laser pulses intermittently emitted toward the eyes of a patient is constant, was exemplified. On the contrary, an ophthalmic laser surgery apparatus 1 of the present modification example condenses the laser pulse on a plurality of condensing positions while changing the energy of each laser pulse emitted toward the eyes of a patient.

In detail, the ophthalmic laser surgery apparatus 1 of the present modification example adjusts the energy of each laser pulse such that fluence (amount of energy per unit area) of the laser pulse condensed on each condensing position is constant (substantially constant). As described above, the aberration fluctuates when the condensing position of the pulse laser light scanned by the scanning unit 30 changes. If the aberration fluctuates when the energy of the laser pulse is constant, the fluence of the laser pulse in each condensing position fluctuates. The ophthalmic laser surgery apparatus 1 of the present modification example adjusts the energy of the laser pulse in consideration of the fluctuation in the aberration such that the fluence becomes constant regardless of the influence of the aberration. As a result, the quality of the surgery improves. For example, in some cases, the amount of light transmitted without being absorbed into the tissue in the vicinity of the condensing position is approximated and the influence of the transmitted light on the eyes of a patient is suppressed. In addition, the energy of the laser pulse may be adjusted such that the fluence at each condensing position coincides to the threshold value for causing a non-linear interaction in the tissue or such that the fluence thereof slightly exceeds the threshold value. In this case, the amount of light transmitted through the tissue decreases regardless of the condensing position, and therefore, the influence of the transmitted light on the eyes of a patient is further suppressed.

It is possible to employ various methods as the method for adjusting the energy of the laser pulse such that the fluence becomes constant. For example, it is possible to adjust the energy such that the fluence becomes constant using data (for example, table data) or an algorithm for determining the condensing position controlled by the scanning unit 30 and the energy of the laser pulse condensed on each condensing position. Similarly to the above-described embodiment, the data or the algorithm may be created using a result of irradiating a sample substance with pulse laser light or may be created using a calculation expression for calculating an approximate value of an aberration. In addition, it is also possible to employ various methods as the method for adjusting the energy of the laser pulse emitted toward a tissue. For example, the ophthalmic laser surgery apparatus 1 may adjust the energy of the laser pulse by adjusting the output of the laser light source 10. In addition, the energy of the laser pulse may be adjusted using an adjustment element (for example, an acousto-optical element (AOM), a rotatable polarization element, and an attenuator) provided on an optical path of pulse laser light.

When the energy of the laser pulse changes, the size of a photodisruption generated at each condensing position fluctuates. In this case, it is desirable to adjust at least one parameter such that the density of a plurality of photodisruptions is uniformly approximated. The ophthalmic laser surgery apparatus 1 of the present modification example determines the energy of each laser pulse such that the fluence becomes constant and adjusts at least one of the speed of scanning the condensing position using the scanning unit 30 and the scanning route depending on the sizes of the photodisruptions generated at the condensing position. The information on the sizes of the photodisruptions may be acquired using the same data or algorithm as that in the above-described embodiment or may be acquired through other methods. As the method for adjusting the scanning speed and the scanning route, it is also possible to employ the same methods as those in the above-described embodiment.

The ophthalmic laser surgery apparatus 1 of the present modification example can be expressed as follows. An ophthalmic laser surgery apparatus, which treats the eyes of a patient by causing a photodisruption by condensing pulse laser light on a tissue of the eyes of a patient, includes a laser light source that emits the pulse laser light; an objective lens that condenses the pulse laser light emitted from the laser light source onto the tissue; scanning means that scans a condensing position of the pulse laser light condensed by the objective lens; scanning control means that controls the scanning of the condensing position using the scanning means; and energy adjusting means which adjusts energy of the pulse laser light condensed on each condensing position such that fluence of the pulse laser light condensed on each condensing position becomes constant regardless of the influence of a fluctuation aberration accompanied by change in the condensing position. The scanning control means adjusts the speed of scanning the condensing position using the scanning means depending on the size of the photodisruption which fluctuates in response to the change in the condensing position.

In the present modification example, it is also possible to employ a technique for adjusting the scanning speed and the scanning route and other techniques (for example, a technique for adjusting a repetition frequency depending on the size of the photodisruption) for reducing the influence of the aberration, instead of the technique for adjusting the scanning speed and the scanning route depending on the size of the photodisruption).

It is also possible to add other modifications to the above-described embodiment or the modification example. First, in the above-described embodiment or the modification example, the case of treating the tissue by causing the photodisruption 5 was exemplified. However, the technique exemplified in the above-described embodiment and the modification example can also be applied to a case of severing a tissue or the like without causing the photodisruption 5. That is, the ophthalmic laser surgery apparatus 1 can employ at least a portion of the technique exemplified in the above-described embodiment and the modification example such that partially severed regions generated in the tissue are appropriately disposed at each condensing position. In addition, the technique exemplified in the present embodiment and the modification example can also be applied to a case of treating sites other than the eyes of a patient E.

The ophthalmic laser surgery apparatus 1 of the above-described embodiment and the modification example previously creates control data such that the scanning speed is adjusted depending on the size of the generated photodisruption 5, and performs treatment in accordance with the created control data. However, the ophthalmic laser surgery apparatus 1 may adjust the scanning speed concurrently with the treatment by acquiring information on the size of the generated photodisruption 5 while actually performing the treatment using the pulse laser light. In this case, the ophthalmic laser surgery apparatus 1 may acquire the size of photodisruption 5 which is actually generated using a tomographic image or the like.

In the above-described embodiment and the modification example, the ophthalmic laser surgery apparatus 1 itself creates the control data with which the ophthalmic laser surgery apparatus 1 treats the eyes of a patient E. However, a device other than the ophthalmic laser surgery apparatus 1 may create the control data. For example, a processor of a personal computer may create the control data by executing a program of creating control data for an ophthalmic surgery. In this case, the ophthalmic laser surgery apparatus 1 may acquire the control data from the personal computer and execute treatment in accordance with the acquired control data.

The ophthalmic laser surgery apparatus 1 may control the scanning of the condensing position considering other pieces of information in addition to the information on the size of the photodisruption 5 fluctuating due to the aberration. For example, the ophthalmic laser surgery apparatus 1 may control the scanning of the condensing position also considering the roughness (smoothness) of a surface to be severed.

The ophthalmic laser surgery apparatus 1 of the above-described embodiment and the modification example adjusts the speed of scanning the condensing position, and the gaps between the scanning routes 7 depending on the size of the photodisruption 5. However, the ophthalmic laser surgery apparatus 1 also can adjust either of the scanning speed or the gaps between the scanning routes 7 depending on the size of the photodisruption 5. Even in this case, the influence of the aberration is reduced. In addition, in the above-described embodiment, the description was made on the premise that the size of the photodisruption 5 becomes smaller as the aberration becomes larger. However, the technique exemplified in the above-described embodiment can be applied as long as the size of the photodisruption 5 fluctuates according to the fluctuation in the aberration. For example, as shown in FIG. 5, when the aberration becomes smaller, in some cases, the photodisruption 5 occurs further on an upstream side (that is, at a position at which the beam diameter is larger than that at the condensing position 82) than the condensing position 82 compared to the case in which the aberration is great. In this case, there is a possibility that the size of the photodisruption 5 may become larger as the aberration becomes smaller. Even in this case, the photodisruptions 5 are appropriately disposed by applying the technique exemplified in the above-described embodiment and the modification example.

What is claimed is:

1. An ophthalmic laser surgery apparatus for treating an eye of a patient, the ophthalmic laser surgery apparatus comprising:
    a laser light source configured to emit the pulse laser light;
    an objective lens configured to condense the pulse laser light emitted from the laser light source on the tissue to cause a photodistuption of the tissue;
    a scanner configured to scan a condensing position of the pulse laser light condensed by the objective lens; and
    a controller configured to control the scanner to adjust speed of scanning the condensing position depending on a size of the photodisruption which fluctuates in according to an aberration which fluctuates according to a change in the condensing position.

2. The ophthalmic laser surgery apparatus according to claim 1,
    wherein the controller adjusts the speed of the scanning such that the speed of scanning the condensing position is decreased as the size of the photodisruption becomes smaller.

3. The ophthalmic laser surgery apparatus according to claim 1,
    wherein the controller sets scanning routes, along which the condensing position moves, such that gaps between the scanning routes are shortened as the size of the photodisruption becomes smaller.

4. The ophthalmic laser surgery apparatus according to claim 1,
    wherein the controller controls the scanner based on one of data and an algorithm for determining a relationship between the condensing position controlled by the scanner, and the size of the photodisruption at each of the condensing positions.

5. The ophthalmic laser surgery apparatus according to claim 1,
    wherein the controller corrects the condensing position of the pulse laser light controlled by the scanner at least in a direction along an optical axis of the pulse laser light according to the aberration which fluctuates according to the change in the condensing position.

6. A method of controlling an ophthalmic laser surgery apparatus for treating an eye of a patient, the method comprising:
    emitting the pulse laser light;
    condense the emitted pulse laser light on the tissue to cause a photodistuption of the tissue;
    scanning a condensing position of the condensed pulse laser light; and
    controlling the scanner to adjust speed of scanning the condensing position depending on a size of the photodisruption which fluctuates in according to an aberration which fluctuates according to a change in the condensing position.

7. A non-transitory computer readable recording medium storing a computer readable instruction for creating control data that controls an ophthalmic laser surgery apparatus which treats eyes of a patient by causing a photodisruption in a tissue by condensing pulse laser light on the tissue of the eyes of the patient, the instruction causing a processer of the ophthalmic laser surgery apparatus to execute:

a creation step of creating control data which causes the ophthalmic laser surgery apparatus to adjust speed of scanning a condensing position using a scanner depending on a size of the photodisruption which fluctuates in response to an aberration accompanied by a change in the condensing position.

* * * * *